US009035100B2

(12) United States Patent
Suwa et al.

(10) Patent No.: US 9,035,100 B2
(45) Date of Patent: May 19, 2015

(54) METHOD FOR PRODUCING PHENYLPHOSPHONIC ACID METAL SALT COMPOSITION, AND CRYSTAL NUCLEATING AGENT THEREFROM

(71) Applicant: NISSAN CHEMICAL INDUSTRIES, LTD., Tokyo (JP)

(72) Inventors: Takeshi Suwa, Funabashi (JP); Hisato Hayashi, Funabashi (JP); Masahiro Hida, Funabashi (JP); Masaaki Ozawa, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/331,881

(22) Filed: Jul. 15, 2014

(65) Prior Publication Data

US 2014/0330038 A1    Nov. 6, 2014

Related U.S. Application Data

(62) Division of application No. 12/878,242, filed on Sep. 9, 2010.
(60) Provisional application No. 61/272,293, filed on Sep. 9, 2009.

(51) Int. Cl.
*C08K 5/5317* (2006.01)
*C07F 9/38* (2006.01)

(52) U.S. Cl.
CPC .............. *C08K 5/5317* (2013.01); *C07F 9/3834* (2013.01)

(58) Field of Classification Search
CPC ........................... C08K 5/5317; C07F 9/3834
USPC ........................................................ 568/17
See application file for complete search history.

(56) References Cited

U.S. PATENT DOCUMENTS

2007/0299170 A1    12/2007    Ozawa et al.

FOREIGN PATENT DOCUMENTS

JP    A-2004-187455    7/2004

*Primary Examiner* — John Uselding
(74) *Attorney, Agent, or Firm* — Oliff PLC

(57) ABSTRACT

A method for producing a phenylphosphonic acid metal salt composition, including reacting a phenylphosphonic acid compound (a) with a metal salt, metal oxide or metal hydroxide (b) that is present in an amount beyond the equivalent, the phenylphosphonic acid metal salt composition containing phenylphosphonic acid metal salt, and a surplus amount of the metal salt, the metal oxide or the surplus metal hydroxide (b). A crystal nucleating agent comprises the phenylphosphonic acid metal salt composition produced by the method.

10 Claims, 4 Drawing Sheets

SEM image of the zinc phenylphosphonate composition prepared in Synthesis Example 4

SEM image of the zinc phenylphosphonate prepared in Comparative Synthesis Example 1

SEM image of the calcium phenylphosphonate composition prepared in Synthesis Example 12

SEM image of the calcium phenylphosphonate prepared in Comparative Synthesis Example 2

METHOD FOR PRODUCING PHENYLPHOSPHONIC ACID METAL SALT COMPOSITION, AND CRYSTAL NUCLEATING AGENT THEREFROM

RELATED APPLICATIONS

The present application is a divisional of application Ser. No. 12/878,242 filed Sep. 9, 2010, which in turn is a nonprovisional of provisional Application No. 61/272,293 filed Sep. 9, 2009. The prior applications are incorporated herein by reference in their entireties.

TECHNICAL FIELD

The present invention relates to a method for producing a phenylphosphonic acid metal salt, a phenylphosphonic acid metal salt composition containing a phenylphosphonic acid metal salt and surplus metal salt, surplus metal oxide or surplus metal hydroxide produced by the method, and a thermoplastic resin composition containing the phenylphosphonic acid metal salt composition.

BACKGROUND ART

Thermoplastic resins, and in particular poly(lactic acid) resins which are biodegradable polyester resins, appear promising for use as packaging materials such as containers and films, as textile materials for garments, floor mats and automotive interior materials, and as molding materials in the production of housings and components for electrical and electronics products. Polyolefin resins are widely used in materials for the necessities of daily life and in various types of industrial components, such as automotive interior and exterior components. The range of polyolefin resin use has grown particularly in automotive interior and exterior components, such as bumpers, instrument panels, door trim and pillars.

In order to improve the processability and heat resistance of thermoplastic resins, including such poly(lactic acid) resins and polyolefin resins, efforts are being made to increase the rate of crystallization and degree of crystallization of these resins. One such approach involves adding a crystal nucleating agent. A "crystal nucleating agent" serves as the primary crystal nuclei for crystalline polymer and promotes crystal growth; hence, it functions to make the crystal size finer and also increases the rate of crystallization.

For example, crystal nucleating agents for poly(lactic acid) resins that have been disclosed include inorganic particles composed of talc and/or boron nitride of having a particle size less than a specific particle size (Patent Document 1), amide compounds of a specific formula (Patent Document 2), sorbitol derivatives of a specific formula (Patent Document 3), phosphoric acid ester metal salts and basic inorganic aluminum compounds (Patent Document 4), and metal salts of phosphorus compounds of a specific formula (e.g., phenylphosphonic acid metal salts) (Patent Document 5).

Also, metal salts of phosphonic acid, phosphonous acid and the like are available as effective crystal nucleating agents for poly(etherester) block copolymers (Patent Document 6).

In addition, carboxylic acid metal salts, such as sodium benzoate, aluminum 4-tert-butylbenzoate, sodium adipate and sodium bicyclo[2.2.1]heptane-2,3-dicarboxylate; phosphoric acid ester metal salts such as sodium bis(4-tert-butylphenyl)phosphate and sodium 2,2'-methylenebis(4,6-di-tert-butylphenyl)phosphate; compounds such as polyol derivatives, including dibenzylidene sorbitol, bis(methylbenzylidene)sorbitol and bis(dimethylbenzylidene)sorbitol; and metal salts of, for example, aromatic phosphonic acids and aromatic phosphonous acids have been proposed as crystal nucleating agents for polyolefins (Patent Document 7).

SUMMARY OF THE INVENTION

Problems to be Solved by the Invention

As mentioned above, methods which use a crystal nucleating agent are useful because they speed up the rate of crystallization and enable the degree of crystallization to be increased. However, in order to achieve a higher processability and heat resistance and utilize the resin compositions in a broad range of applications, there has existed a desire recently for the development of more effective crystal nucleating agents.

When use is made of the metal salts of phosphorus compounds (e.g., metal salts of phenylphosphonic acids) which, even among the above crystal nucleating agents, are regarded as having an excellent performance, in order to reduce the environmental load, it is desirable as well to lower the content of organic ingredients (i.e., the content of phenylphosphonic acid) included in the crystal nucleating agent.

It is therefore an object of the present invention to provide a method for producing crystal nucleating agents highly suitable for promoting the crystallization of thermoplastic resins, including poly(lactic acid) resins and polyolefin resins, and particularly a method for producing phenylphosphonic acid metal salts which are highly suitable as crystal nucleating agents that reduce the amount of petroleum-derived organic ingredients having a high environmental load.

Further objects of the present invention are to provide phenylphosphonic acid metal salt compositions which contain a phenylphosphonic acid metal salt produced by the above-mentioned method, crystal nucleating agents comprising the phenylphosphonic acid metal salt composition, and thermoplastic resin compositions comprising the phenylphosphonic acid metal salt composition and a thermoplastic resin.

Means for Solving the Problems

The inventors have conducted extensive investigations in order to overcome the above-mentioned problems. As a result, they have discovered that, in the production of phenylphosphonic acid metal salts, which are useful as crystal nucleating agents, by reacting a phenylphosphonic acid compound with a metal salt, metal oxide or metal hydroxide (these are referred to collectively below also as "metallic compounds") that is present in an amount beyond the equivalent relative to the phenylphosphonic acid compound, the shape of the metal salt which is obtained (which separates out) can be made smaller than the shape obtained by conventional production methods, thus enabling a higher activity as a crystal nucleating agent to be achieved, and then completed the present invention.

That is, in a first aspect the present invention relates to a method for producing a phenylphosphonic acid metal salt composition, which comprises reacting a phenylphosphonic acid compound (a) of formula [1]

[Chemical Formula 1]

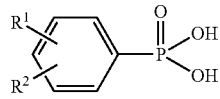

[1]

in which $R^1$ and $R^2$ are independently of each other hydrogen atom, $C_{1-10}$ alkyl or $C_{1-10}$ alkoxycarbonyl, with a metal salt, metal oxide or metal hydroxide (b) that is present in an amount beyond the equivalent, wherein the phenylphosphonic acid metal salt composition contains phenylphosphonic acid metal salt, and a surplus amount of the metal salt, the metal oxide or the surplus metal hydroxide (b).

In a second aspect, the present invention relates to a crystal nucleating agent comprising the phenylphosphonic acid metal salt composition produced by the method of the first aspect.

Additional aspects of the claimed invention are described below.

Effects of the Invention

According to the present invention, by reacting a phenylphosphonic acid compound with a metal salt, metal oxide or metal hydroxide that is present in an amount beyond the equivalent with respect to the phenylphosphonic acid compound, and in particular by carrying out such a reaction in a solvent that hardly dissolves the metal salt, metal oxide or metal hydroxide, the metal salt which is thereby obtained (which separates out) can be rendered into a much finer shape than the shape obtained by a conventional production method involving the reaction of a phenylphosphonic acid compound with an equivalent amount of a metal salt, metal oxide or metal hydroxide, thus enabling the activity as a crystal nucleating agent to be greatly enhanced.

That is, the production method of the present invention is capable of producing a phenylphosphonic acid metal salt in a much finer shape than that obtained in accordance with conventional production methods, without requiring additional steps such as grinding. Moreover, although the reason why it is possible to obtain a finer shape than with conventional production methods is not well understood, it is thought that the phenylphosphonic acid metal salt which has formed near the surface of the metallic compound particles or elsewhere in the solvent crystallizes at the surface of the metallic compound particles, and some or all of the crystallized phenylphosphonic acid metal salt peels and falls off, yielding a finer shape.

In addition, the phenylphosphonic acid metal salt produced by the production method of the present invention has a finer shape than the phenylphosphonic acid metal salt obtained by conventional production methods. For this reason, when a phenylphosphonic acid metal salt composition containing the above-mentioned phenylphosphonic acid metal salt and surplus metal salt, surplus metal oxide or surplus metal hydroxide is used as a crystal nucleating agent during the production of a thermoplastic resin such as a polyester resin (e.g., poly(lactic acid) resin) or a crystalline polyolefin resin, the crystallization promoting effect of these resins can be enhanced, which in turn makes it possible to provide thermoplastic resin compositions having an excellent heat resistance and processability.

EMBODIMENTS

Figure 1:
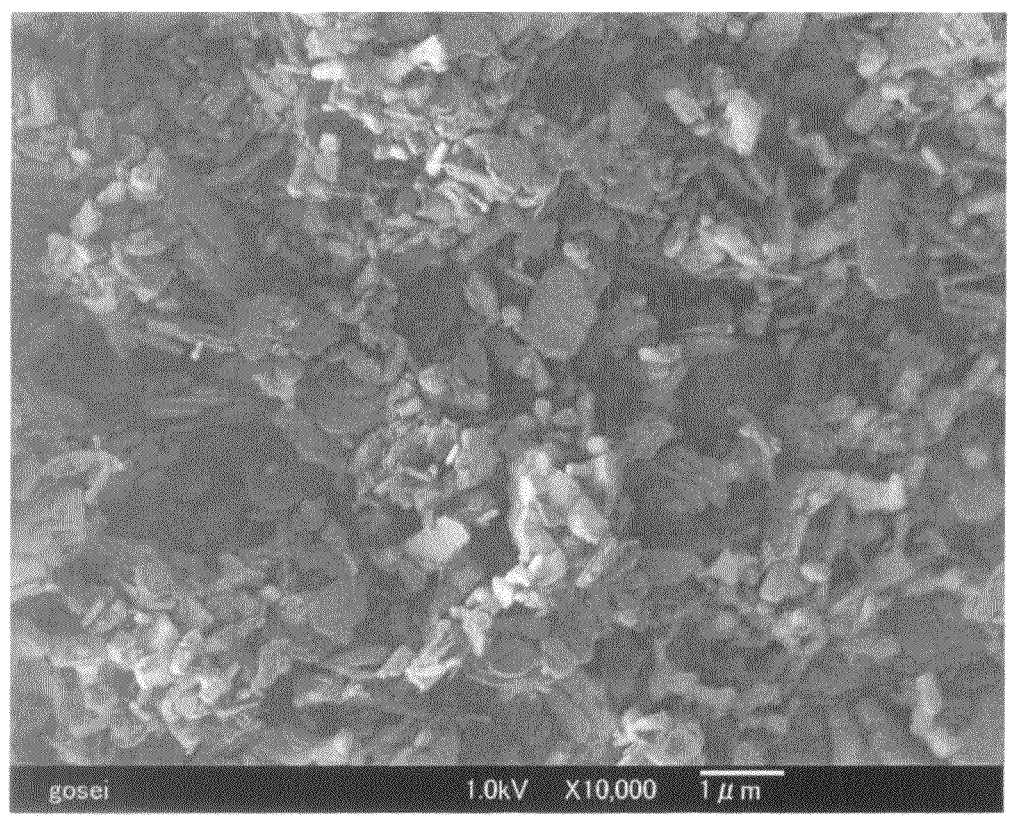
FIG. 1 is a micrograph with scanning electron microscope (SEM) of the white powder of zinc phenylphosphonate-containing zinc oxide (molar ratio: PPA–Zn/ZnO=10/90) prepared in Synthesis Example 4.

A method for producing a phenylphosphonic acid metal salt according to the present invention is characterized by reacting a phenylphosphonic acid compound with a metallic compound (metal salt, metal oxide or metal hydroxide) that is present in an amount beyond the equivalent with respect to the phenylphosphonic acid compound, and in particular carrying out the reaction in a solvent that hardly dissolves the metallic compound.

The present invention is described in more detail below.

The phenylphosphonic acid compound used in the production method of the present invention is a compound of general formula [1] below.

[Chemical Formula 2]

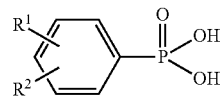

[1]

In the phenylphosphonic acid compound of the formula [1], $R^1$ and $R^2$ are independently of each other hydrogen atom; a $C_{1-10}$alkyl such as methyl, ethyl, n-propyl, isopropyl, n-butyl, isobutyl or tert-butyl; or a $C_{1-10}$ alkoxycarbonyl such as methoxycarbonyl or ethoxycarbonyl. $R^1$ and $R^2$ may be the same or different.

Illustrative examples of the phenylphosphonic acid compound of the formula [1] include phenylphosphonic acid, 4-methylphenylphosphonic acid, 4-ethylphenylphosphonic acid, 4-n-propylphenylphosphonic acid, 4-isopropylphenylphosphonic acid, 4-n-butylphenylphosphonic acid, 4-isobutylphenylphosphonic acid, 4-tert-butylphenylphosphonic acid, 3,5-dimethoxycarbonylphenylphosphonic acid, 3,5-diethoxycarbonylphenylphosphonic acid, 2,5-dimethoxycarbonylphenylphosphonic acid and 2,5-diethoxycarbonylphenylphosphonic acid.

As these compounds, commercial products can be used without modification.

The metal salt used in the production method of the present invention is not subject to any particular limitation. For example, use may be made of sulfates, nitrates, chlorides, carbonates and acetates.

The metal used in the metal salt, metal oxide or metal hydroxide may be a monovalent, divalent or trivalent metal. The metal in these metallic compounds may be used as a mixture of two or more different metals. Illustrative examples of the metal include lithium, sodium, potassium, magnesium, aluminum, calcium, barium, manganese, iron, cobalt, nickel, copper and zinc. Of these, lithium, sodium, potassium, magnesium, calcium, barium, manganese, iron, cobalt, copper and zinc are preferred as the metal. Zinc and calcium are especially preferred. Specifically, it is preferable to use zinc oxide or calcium carbonate.

Suitable use may be also made of a commercial product without modification as these metallic compounds, i.e., the metal salt, metal oxide or metal hydroxide.

The reaction of the phenylphosphonic acid compound with the metallic compound is carried out in a suitable medium and using the metallic compound in an amount beyond the equivalent with respect to the phenylphosphonic acid compound.

The medium used here is not subject to any particular limitation. However, from the standpoint of reaction efficiency, it is preferably a medium in which the phenylphosphonic acid compound serving as a starting material is soluble. Also, taking into consideration the recovery of the final product, the medium is preferably a solvent that hardly dissolves the metallic compound serving as a starting material and the phenylphosphonic acid metal salt.

Illustrative examples of the solvents include water; ketones such as acetone, methyl ethyl ketone and methyl isobutyl ketone; nitriles such as acetonitrile; ethers such as tetrahydrofuran; alcohols such as methanol, ethanol, 1-propanol and 2-propanol; amides such as N,N-dimethylformamide, N,N-dimethylacetamide and N-methyl-2-pyrrolidone; and sulfoxides such as dimethyl sulfoxide. These solvents may be used singly or as mixtures of two or more thereof. Of the above, the use of water or an alcohol is preferred. From the standpoint of handling ease and economic considerations, the use of water is more preferred.

In the above-mentioned reaction, total charged amount of the medium is preferably 0.001 to 1,000 times total charged amount of the phenylphosphonic acid compound (a) and the metallic compound (b). The lower limit of the total charged amount of the medium is more preferably 0.002 time, most preferably. 0.01 time total charged amount of the phenylphosphonic acid compound (a) and the metallic compound (b). The upper limit of the total charged amount of the medium is more preferably 200 times, most preferably 100 times, further preferably 50 times total charged amount of the phenylphosphonic acid compound (a) and the metallic compound (b).

In the meantime, it is possible to mix the phenylphosphonic acid compound (a) and the metallic compound (b) without use of the medium. In that case, however, the progress of the reaction becomes extremely slow and thus the reaction becomes industrially disadvantageous. On the other hand, in case where the medium is used in too excess amount, volume efficiency becomes low, and thus the reaction also becomes industrially disadvantageous.

In the above-mentioned reaction, it is preferable for the phenylphosphonic acid compound and the metallic compound to be charged in amounts, expressed as the molar ratio of the metallic compound (b) to the phenylphosphonic acid compound (a), of 100:0.01 to 100:90. The upper limit in the amount of phenylphosphonic acid compound (a) charged, expressed as the molar ratio of the metallic compound (b) to the phenylphosphonic acid compound (a), is more preferably (b):(a)=100:80, and even more preferably (b):(a)=100:70. The lower limit in the amount of phenylphosphonic acid compound (a) charged, expressed as the molar ratio of the metallic compound (b) to the phenylphosphonic acid compound (a), is more preferably (b):(a)=100:0.1, even more preferably (b):(a)=100:1, and most preferably (b):(a)=100:2.

Regarding the actual procedure for carrying out the reaction, the reaction may be carried out by, for example, a method of adding a solution of the phenylphosphonic acid compound to a slurry containing the metallic compound serving as a starting material, a method of adding a solution of the phenylphosphonic acid compound to the metallic compound, a method of adding a solvent in a mixture of the metallic compound and the phenylphosphonic acid compound, and the like. The solvent used here in the slurry or the phenylphosphonic acid compound solution, and the solvent to be added may be any of the above-mentioned media.

In addition, as the reaction apparatus, any apparatuses that can provide sufficient flow of the reaction system can be used without any limitation, and they include in addition to reaction vessel equipped with a stirring element, several mixers such as a homomixer, Henschel mixer, Loedige mixer or the like, several mills such as a ball mill, bead mill, Ultimizer or the like. When a mixer that is excellent in mixing property of powders and can carry out mixing, heating and the like simultaneously or sequentially, for example Henschel mixer, Loedige mixer or the like is used, it becomes possible to significantly reduce the amount of the medium to be used, volume efficiency is improved, and further reaction and the dry described below can be carried out in the same apparatus. Thus, the use of such a mixer provides industrial advantage.

To obtain a powder in which the resulting phenylphosphonic acid metal salt is uniformly dispersed in the surplus amount of the metallic compound serving as a starting material, it is preferable to add the solution or the solvent in a dropwise manner or at one time while the slurry, the metallic compound or the mixture is stirred with a stirring element or the like.

The reaction temperature at this time may have an influence on the size of the resulting phenylphosphonic acid metal salt. That is, at a higher reaction temperature, the phenylphosphonic acid metal salt which separates out has a higher solubility, which leads to an increase in the size of the crystals at the time of recrystallization. Therefore, to achieve the object of the present invention, which is to obtain phenylphosphonic acid metal salt having a fine shape, it is desirable to keep the temperature of the above reaction at 30° C. or less.

Following completion of the reaction, the medium is removed by filtration or distillation, following which drying is carried out, thereby giving a phenylphosphonic acid metal salt composition containing a phenylphosphonic acid metal salt and surplus metal salt, surplus metal oxide or surplus metal hydroxide (also referred to below as "surplus metallic compound"). The phenylphosphonic acid metal salt composition may have a form in which particles of the phenylphosphonic acid metal salt are dispersed in clusters of particles of the metallic compound serving as a starting material; that is, the composition may be in the form of a crystalline powder of a metal salt, metal oxide or metal hydroxide in which the phenylphosphonic acid metal salt are dispersed. Complexes of phenylphosphonic acid metal salt adhered to some or all surfaces of the metallic compound particles may also be included.

The drying temperature at this time may be suitably selected according to the type of medium. Reduced-pressure conditions may also be suitably used.

When water is employed as the medium, the drying temperature at standard pressure is preferably from 100 to 500° C., and more preferably from 120 to 200° C. At a temperature less than 100° C., the water of crystallization cannot be completely eliminated and takes the form of a monohydrate of the phenylphosphonic acid metal salt, which is unsuitable for use as a crystal nucleating agent for resins that are adversely affected by hydrolysis (e.g., polyester resins) and is thus undesirable. On the other hand, at temperatures more than 500° C., there is a concern that decomposition of the phenylphosphonic acid metal salt will be induced.

The phenylphosphonic acid metal salt of the present invention obtained by the above-described production method has a very fine shape. For example, zinc phenylphosphonate has a very fine granular shape with an average particle size of from 0.05 to 1 μm, and preferably from 0.05 to 0.5 μm. Calcium phenylphosphonate is shaped as very small needles with an average thickness of from 0.05 to 1 μm, and preferably from 0.05 to 0.5 μm.

If necessary, the metal salt, metal oxide or metal hydroxide in which the phenylphosphonic acid metal salt thus obtained is dispersed may be rendered into an even finer shape using a mixer that applies a shear strength, such as a homomixer, a Henschel mixer or a Loediger mixer; or using a grinding mill such as a ball mill, pin disc mill, pulverizer, Inomizer or counter jet mill. Alternatively, a finer shape can also be achieved with a wet mill that employs water, an organic solvent miscible with water, or a mixed solution thereof, such as a ball mill, bead mill, sand grinder, attritor or Ultimizer.

The present invention also relates to a crystal nucleating agent comprising a phenylphosphonic acid metal salt composition comprising a phenylphosphonic acid metal salt and surplus metal salt, surplus metal oxide or surplus metal hydroxide produced by the above-described production method.

The present invention further relates to a thermoplastic resin composition which includes both a phenylphosphonic acid metal salt composition comprising a phenylphosphonic acid metal salt and surplus metal salt, surplus metal oxide or surplus metal hydroxide produced by the above-described production method, and a thermoplastic resin.

Illustrative examples of the above-described thermoplastic resins include general-purpose thermoplastic resins, general-purpose thermoplastic engineering plastics, and biodegradable resins represented by poly(lactic acid) resins.

Illustrative examples of general-purpose thermoplastic resins include polyolefin resins such as polyethylene (PE), polyethylene copolymer, polypropylene (PP), polypropylene copolymer, polybutylene (PB), ethylene-vinyl acetate copolymer (EVA), ethylene-ethyl acrylate copolymer (EEA) and poly(4-methyl-1-pentene); polystyrene resins such as polystyrene (PS), high-impact polystyrene (HIPS), acrylonitrile-styrene copolymer (AS) and acrylonitrile-butadiene-styrene copolymer (ABS); and vinyl chloride resins, polyurethane resins, phenolic resins, epoxy resins, amino resins and unsaturated polyester resins, and the like.

Illustrative examples of general-purpose engineering plastics include polyamide resins, polycarbonate resins, poly(phenylene ether) resins, modified poly(phenylene ether) resins, polyester resins such as poly(ethylene terephthalate) (PET) and poly(butylene terephthalate) (PBT), polyacetal resins, polysulfone resins, poly(phenylene sulfide) resins and polyimide resins.

The poly(lactic acid) resins include homopolymers and copolymers of poly(lactic acid). When the poly(lactic acid) resin is a copolymer, the copolymer may be any one of a random copolymer, alternating copolymer, block copolymer or graft copolymer. Alternatively, the copolymer may be a blend polymer with other resin, which blend copolymer is composed primarily of a poly(lactic acid) homopolymer or copolymer. Illustrative examples of the other resin include the subsequently described biodegradable resins other than poly(lactic acid) resins, and the above-mentioned general-purpose thermoplastic resins and general-purpose thermoplastic engineering plastics.

The poly(lactic acid) resins, while are not subject to any particular limitation, are exemplified by lactides that have been subjected to ring-opening polymerization, and D-lactic acid, L-lactic acid, racemic lactic acid or the like which has been directly polycondensed. The poly(lactic acid) resins have a number average molecular weight of generally from about 10,000 to about 500,000. Poly(lactic acid) resins that may be used include ones that have been crosslinked with a crosslinking agent using heat, light, radiation or the like.

Illustrative examples of biodegradable resins other than poly(lactic acid) resins include polyhydroxyalkanoic acids such as poly(3-hydroxybutyric acid) and copolymers of 3-hydroxybutyric acid and 3-hydroxyhexanoic acid, polycaprolactone, poly(butylene succinate), poly(butylene succinate/adipate), poly(butylene succinate/carbonate), poly(ethylene succinate), poly(ethylene succinate/adipate), poly(vinyl alcohol), poly(glycolic acid), modified starches, cellulose acetate, chitin, chitosan and lignin.

The phenylphosphonic acid metal salt composition comprising phenylphosphonic acid metal salt and surplus metal salt, surplus metal oxide or surplus metal hydroxide is included in the above thermoplastic resin composition in an amount of preferably from 0.01 to 10 parts by mass, more preferably from 0.02 to 5 parts by mass, and even more preferably from 0.03 to 2 parts by mass, based on 100 parts by mass of the thermoplastic resin. If the phenylphosphonic acid metal salt composition is included in an amount less than 0.01 part by mass, adequately increasing the crystallization rate of the thermoplastic resin will be difficult. On the other hand, at more than 10 parts by mass, a thermoplastic resin having a rapid crystallization rate can be obtained but a further increase in the rate of crystallization is not achieved.

In the present invention, the method for blending the phenylphosphonic acid metal salt composition comprising a phenylphosphonic acid metal salt and surplus metallic compound (surplus metal salt, surplus metal oxide or surplus metal hydroxide) into the thermoplastic resin is not subject to any particular limitation, and may be carried out by a known method. For example, the thermoplastic resin and the phenylphosphonic acid metal salt composition comprising a phenylphosphonic acid metal salt and surplus metallic compound may each be mixed in respective mixers, then kneaded together using a single-screw or twin-screw extruder or the like. Kneading is generally carried out at a temperature of about 150 to 220° C. Alternatively, a method that comprises preparing a masterbatch which includes the phenylphosphonic acid metal salt composition comprising a phenylphosphonic acid metal salt and surplus metallic compound in a high concentration, and adding the masterbatch to a thermoplastic resin is also possible. Yet another method that may be used is to add the phenylphosphonic acid metal salt composition comprising a phenylphosphonic acid metal salt and surplus metallic compound at the stage of thermoplastic resin polymerization.

Known inorganic fillers may be used in the thermoplastic resin composition of the present invention. Illustrative examples of such fillers include glass fibers, carbon fibers, talc, mica, silica, kaolin, clay, wollastonite, glass beads, glass flakes, potassium titanate, calcium carbonate, magnesium sulfate and titanium oxide. These inorganic fillers may have a shape which is fibrous, granular, laminar, needle-like, spherical or powdered. Such inorganic fillers may be used in an amount of up to 300 parts by mass based on 100 parts by mass of the thermoplastic resin.

Known fire retardants may be used in the thermoplastic resin composition of the present invention. Illustrative examples include halogen-based fire retardants such as bromine- or chlorine-based fire retardants, antimony-based fire retardants such as antimony trioxide or antimony pentaoxide, inorganic fire retardants such as aluminum hydroxide, magnesium hydroxide or silicone compounds, phosphorus-based fire retardants such as red phosphorus, phosphoric acid esters, ammonium polyphosphate or phosphazene, melamine-based fire retardants such as melamine, melam, melem, melon, melamine cyanurate, melamine phosphate, melamine pyrophosphate, melamine polyphosphate, polyphosphoric acid-melamine-melam-melem complex salts, melamine alkylphosphonates, melamine phenylphosphonate, melamine sulfate or melam methanesulfonate, and fluorocarbon resins such as PTFE. These fire retardants may be used in an amount of up to 200 parts by mass based on 100 parts by mass of the thermoplastic resin.

Aside from the above ingredients, concomitant use may also be made of various additives customarily used in the production of ordinary synthetic resins, such as heat stabilizers, light stabilizers, ultraviolet absorbers, antioxidants, impact modifiers, antistatic agents, pigments, colorants, parting agents, lubricants, plasticizers, compatibilizing agents, blowing agents, fragrances, antimicrobial/antifungal agents, various types of coupling agents such as silane-, titanium-, and aluminum-based coupling agents, various other types of fillers, and other crystal nucleating agents.

Ordinary molding methods such as injection molding, blow molding, vacuum molding and compression molding may be employed on the thermoplastic resin composition of the present invention. Various types of molded articles can be easily obtained by such molding methods.

EXAMPLES

The present invention is further concretely described below by way of examples to which the present invention is limited.

Synthesis Example 1

An aqueous slurry of zinc oxide was prepared by charging a 300 mL reaction flask equipped with a stirrer with 10.0 g (123 mmol) of zinc oxide (JIS grade 2, available from HakusuiTech Ltd.) and 90.0 g of water. An aqueous solution of 13.6 g (86 mmol) of phenylphosphonic acid (available from Nissan Chemical Industries, Ltd.) dissolved in 77.0 g of water was gradually added dropwise at room temperature (about 25° C.) to this slurry with stirring, thereby effecting a reaction for one hour. The slurry was then filtered, and the wet cake was thoroughly rinsed with water. The wet cake was subsequently dried at 120° C. for at least 12 hours, yielding a white powder of zinc phenylphosphonate-containing zinc oxide.

Synthesis Examples 2 to 8

In each of these examples, aside from using phenylphosphonic acid (PPA) and water in the amounts indicated in Table 1 as the aqueous solution of phenylphosphonic acid, synthesis was carried out in the same way as in Synthesis Example 1, giving a white powder of zinc phenylphosphonate-containing zinc oxide.

FIG. 1 shows a micrograph taken with a field-emission scanning electron microscope (SEM: JSM-7400F, manufactured by JEOL Ltd.) of the white powder of zinc phenylphosphonate-containing zinc oxide produced in Synthesis Example 4.

Comparative Synthesis Example 1

Figure 2:
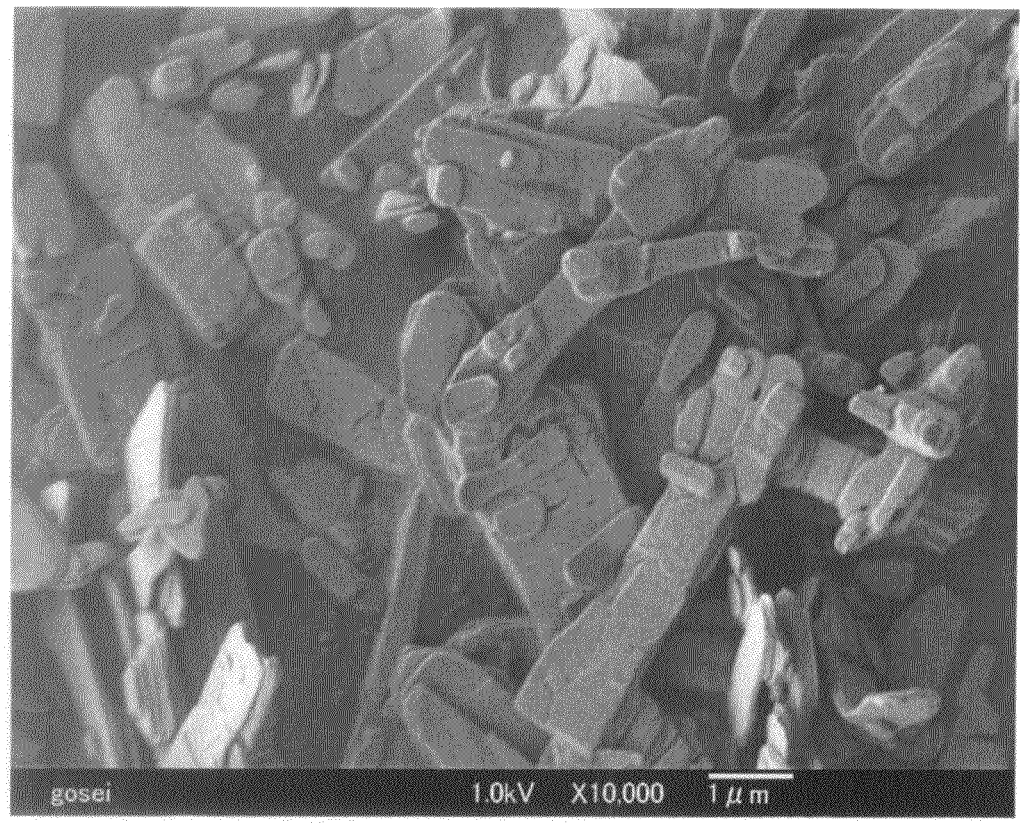
FIG. 2 is a micrograph with scanning electron microscope (SEM) of the white powder of zinc phenylphosphonate prepared in Comparative Synthesis Example 1.

An aqueous slurry of zinc oxide was prepared by charging a 300 mL reaction flask equipped with a stirrer with 10.0 g (123 mmol) of zinc oxide (JIS grade 2, available from HakusuiTech Ltd.) and 90.0 g of water. An aqueous solution of 19.4 g (123 mmol) of phenylphosphonic acid (Nissan Chemical Industries, Ltd.) dissolved in 110.0 g of water was gradually added dropwise at room temperature (about 25° C.) to this slurry with stirring, thereby effecting a reaction for five hours. The slurry was then filtered and the wet cake was thoroughly rinsed with water. The wet cake was subsequently dried at 120° C. for at least 12 hours, yielding a white powder of zinc phenylphosphonate. FIG. 2 shows a micrograph taken with a field-emission scanning electron microscope (SEM: JSM-7400F, manufactured by JEOL Ltd.) of the white powder of zinc phenylphosphonate thus obtained.

Table 1 shows the aqueous solution of phenylphosphonic acid (PPA) and the molar ratio charged of the phenylphosphonic acid/zinc oxide, which were used in Synthesis Examples 1 to 8 and Comparative Synthesis Example 1.

TABLE 1

| | Aqueous solution of PPA | | |
|---|---|---|---|
| | Amount of PPA used (g) | Amount of $H_2O$ used (g) | PPA/ZnO molar ratio charged |
| Synthesis Example 1 | 13.6 | 77.0 | 70/100 |
| Synthesis Example 2 | 9.7 | 55.0 | 50/100 |
| Synthesis Example 3 | 5.8 | 33.0 | 30/100 |
| Synthesis Example 4 | 1.9 | 11.0 | 10/100 |
| Synthesis Example 5 | 1.4 | 7.7 | 7/100 |
| Synthesis Example 6 | 1.0 | 5.5 | 5/100 |
| Synthesis Example 7 | 0.6 | 3.3 | 3/100 |
| Synthesis Example 8 | 0.2 | 1.1 | 1/100 |
| Comparative Synthesis Example 1 | 19.4 | 110.0 | 100/100 |

Synthesis Example 17

A slurry in ethanol-water of zinc oxide was prepared by charging a 300 mL reaction flask equipped with a stirrer with 10.0 g (123 mmol) of zinc oxide (JIS grade 2, available from HakusuiTech Ltd.) and 90.0 g of 50% by mass ethanol-water. A solution of 1.9 g (12 mmol) of phenylphosphonic acid (Nissan Chemical Industries, Ltd.) dissolved in 11.0 g of 50% by mass ethanol-water was gradually added dropwise at room temperature (about 25° C.) to this slurry with stirring, thereby effecting a reaction for one hour. The slurry was then filtered and the wet cake was thoroughly rinsed with ethanol. The wet cake was subsequently dried at 120° C. for at least 12 hours, yielding a white powder of zinc phenylphosphonate-containing zinc oxide.

Synthesis Example 18

Aside from changing 50% by mass ethanol-water to 75% by mass ethanol-water, synthesis was carried out in the same way as in Synthesis Example 17, giving a white powder of zinc phenylphosphonate-containing zinc oxide.

Synthesis Example 19

Aside from changing 50% by mass ethanol-water to 90% by mass ethanol-water, synthesis was carried out in the same way as in Synthesis Example 17, giving a white powder of zinc phenylphosphonate-containing zinc oxide.

Synthesis Example 20

Aside from changing 50% by mass ethanol-water to ethanol, synthesis was carried out in the same way as in Synthesis Example 17, giving a white powder of zinc phenylphosphonate-containing zinc oxide.

Synthesis Example 21

A slurry in methanol-water of zinc oxide was prepared by charging a 300 mL reaction flask equipped with a stirrer with 10.0 g (123 mmol) of zinc oxide (JIS grade 2, available from HakusuiTech Ltd.) and 90.0 g of 50% by mass methanol-water. A solution of 1.9 g (12 mmol) of phenylphosphonic acid (Nissan Chemical Industries, Ltd.) dissolved in 11.0 g of 50% by mass methanol-water was gradually added dropwise at room temperature (about 25° C.) to this slurry with stirring, thereby effecting a reaction for one hour. The slurry was then filtered and the wet cake was thoroughly rinsed with methanol. The wet cake was subsequently dried at 120° C. for at least 12 hours, yielding a white powder of zinc phenylphosphonate-containing zinc oxide.

Synthesis Example 22

In Loedige mixer (M-20 type (total volume: 20 L) available from Loedige), 5.67 kg (70 mol) of zinc oxide powder (JIS grade 2, available from HakusuiTech Ltd.) and 1.11 kg (7 mol) of phenylphosphonic acid powder (Nissan Chemical Industries, Ltd.) were placed. While mixing these powders, 0.72 kg of water was sprayed thereto over 1 minute (solid concentration in total mixture: 90% by mass), and further mixed for 5 minutes. Then, the mixture was dried for 90 minutes with mixing by flowing steam at 150° C. in the jacket provided with the apparatus surface, yielding a white powder of zinc phenylphosphonate-containing zinc oxide.

Synthesis Example 23

In Loedige mixer (M-20 type (total volume: 20 L) available from Loedige), 8.51 kg (105 mol) of zinc oxide powder (JIS grade 2, available from HakusuiTech Ltd.) was placed. An aqueous solution of 1.67 kg (10.5 mol) of phenylphosphonic acid powder (Nissan Chemical Industries, Ltd.) dissolved in 9.43 kg of water was added thereinto (solid concentration in total mixture: 52% by mass). The resulting mixture was mixed for 5 minutes. Then, the mixture was dried for 60 minutes with mixing by flowing steam at 150° C. in the jacket provided with the apparatus surface and further dried for 70 minutes under reduced pressure, yielding a white powder of zinc phenylphosphonate-containing zinc oxide.

Synthesis Example 9

An aqueous slurry of calcium carbonate was prepared by charging a 300 mL reaction flask equipped with a stirrer with 10.0 g (100 mmol) of calcium carbonate (Escalon #2300 (average particle size, 1.7 μm), available from Sankyo Seifun KK) and 90.0 g of water. An aqueous solution of 11.1 g (70 mmol) of phenylphosphonic acid (Nissan Chemical Industries, Ltd.) dissolved in 62.7 g of water was gradually added dropwise at room temperature (about 25° C.) to this slurry with stirring, thereby effecting a reaction for one hour. The slurry was then filtered and the wet cake was thoroughly rinsed with water. The wet cake was subsequently dried at 200° C. for at least 12 hours, yielding a white powder of calcium phenylphosphonate-containing calcium carbonate.

Synthesis Examples 10 to 16

Aside from using phenylphosphonic acid (PPA) and water in the amounts indicated in Table 2 as the aqueous solution of phenylphosphonic acid, synthesis was carried out in the same way as in Synthesis Example 9, giving a white powder of calcium phenylphosphonate-containing calcium carbonate.

Figure 3:
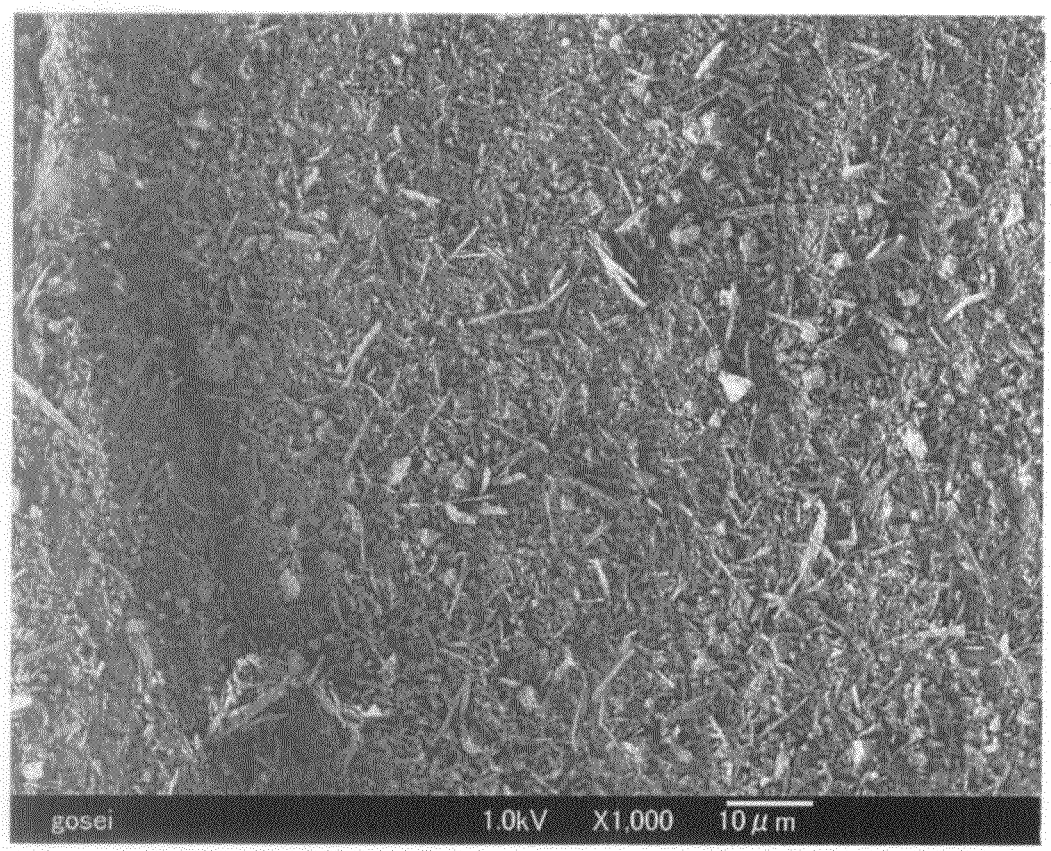
FIG. 3 is a micrograph with scanning electron microscope (SEM) of the white powder of calcium phenylphosphonate-containing calcium carbonate (molar ratio: PPA–Ca/$CaCO_3$=10/90) prepared in Synthesis Example 12.

FIG. 3 shows a micrograph taken with a field-emission scanning electron microscope (SEM: JSM-7400F, manufactured by JEOL Ltd.) of the white powder of calcium phenylphosphonate-containing calcium carbonate produced in Synthesis Example 12.

Comparative Synthesis Example 2

Figure 4:
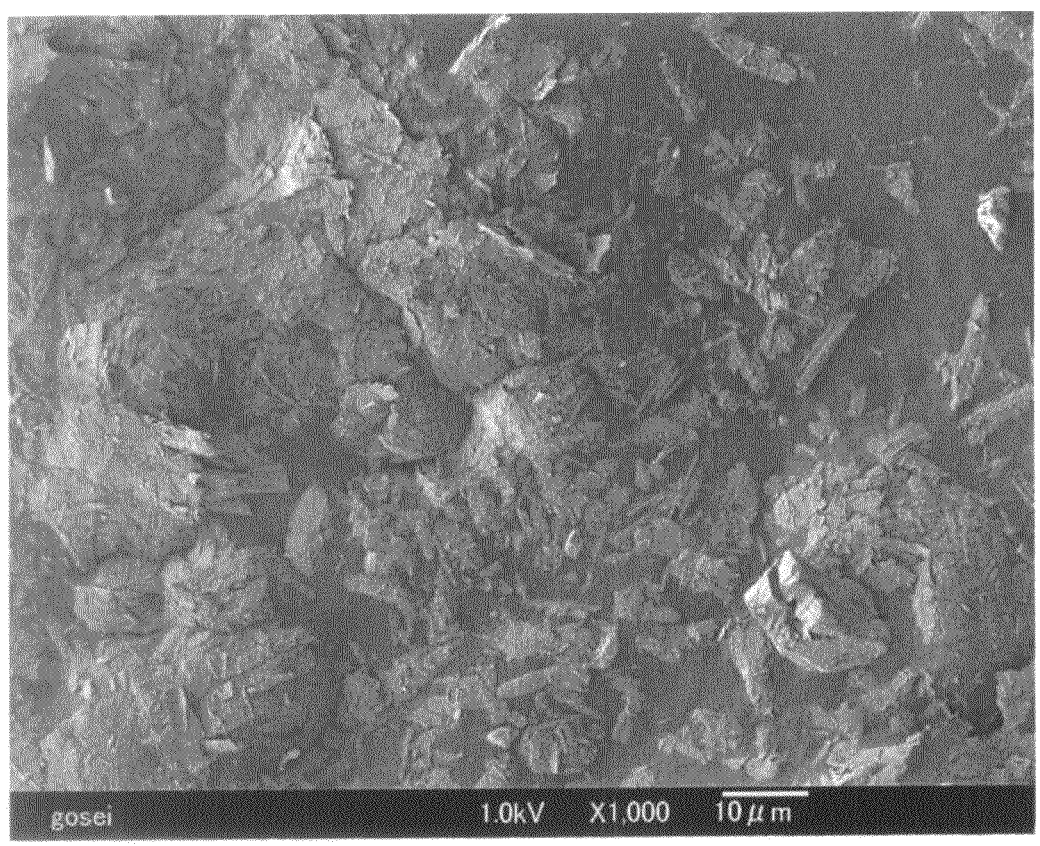
FIG. 4 is a micrograph with scanning electron microscope (SEM) of the white powder of calcium phenylphosphonate prepared in Comparative Synthesis Example 2.

An aqueous slurry of calcium carbonate was prepared by charging a 300 mL reaction flask equipped with a stirrer with 10.0 g (100 mmol) of calcium carbonate (Escalon #2300 (average particle size, 1.7 μm), available from Sankyo Seifun KK) and 90.0 g of water. An aqueous solution of 15.8 g (100 mmol) of phenylphosphonic acid (Nissan Chemical Industries, Ltd.) dissolved in 89.5 g of water was gradually added dropwise at room temperature (about 25° C.) to this slurry with stirring, thereby effecting a reaction for one hour. The slurry was then filtered and the wet cake was thoroughly rinsed with water. The wet cake was subsequently dried at 200° C. for at least 12 hours, yielding a white powder of calcium phenylphosphonate. FIG. 4 shows a micrograph taken with a field-emission scanning electron microscope (SEM: JSM-7400F, manufactured by JEOL Ltd.) of the white powder of calcium phenylphosphonate thus obtained.

Table 2 shows the aqueous solution of phenylphosphonic acid (PPA) and the molar ratio charged of the phenylphosphonic acid/calcium carbonate, which were used in Synthesis Examples 9 to 16 and Comparative Synthesis Example 2.

TABLE 2

| | Aqueous solution of PPA | | |
|---|---|---|---|
| | Amount of PPA used (g) | Amount of H$_2$O used (g) | PPA/CaCO$_3$ molar ratio charged |
| Synthesis Example 9 | 11.1 | 62.7 | 70/100 |
| Synthesis Example 10 | 7.9 | 44.8 | 50/100 |
| Synthesis Example 11 | 4.7 | 26.9 | 30/100 |
| Synthesis Example 12 | 1.6 | 9.0 | 10/100 |
| Synthesis Example 13 | 1.1 | 6.3 | 7/100 |
| Synthesis Example 14 | 0.8 | 4.5 | 5/100 |
| Synthesis Example 15 | 0.5 | 2.7 | 3/100 |
| Synthesis Example 16 | 0.2 | 0.9 | 1/100 |
| Comparative Synthesis Example 2 | 15.8 | 89.5 | 100/100 |

Examples 1 to 8, 30 and 31

In each example, a 5% by mass poly(lactic acid) solution was prepared by adding 1,900 parts by mass of chloroform to 100 parts by mass of poly(lactic acid) resin (U'z S-09, available from Toyota Motor Corporation) and dissolving the resin. One part by mass of the zinc phenylphosphonate-containing zinc oxide obtained in Synthesis Examples 1 to 8, 22 and 23 was added as the crystal nucleating agent to the entire amount of this solution. The crystal nucleating agent was dispersed in the solution by sonicating the resulting mixture for 30 minutes, stirring for 3 hours, then sonicating again for 30 minutes. The resulting solution was then cast onto a Petri dish and the solvent was removed at 50° C. on a hot plate, thereby giving a poly(lactic acid) film in which crystal nucleating agent has been dispersed. This sample was cut up into small pieces, and differential scanning calorimetry (DSC) was carried out (ThermoPlus2 DSC8230, manufactured by Rigaku Corporation). Measurement was carried out by increasing the temperature to 200° C. at 10° C./min, holding the temperature at that level for 5 minutes, then cooling at 5° C./min. The crystallization temperature $T_C$ from the peak temperature of the exotherm which is attributable to poly(lactic acid) crystallization and is observed at the time of cooling was measured. The results are shown in Table 3.

Comparative Example 1

Aside from using 1 part by mass of zinc oxide (JIS grade 2, available from HakusuiTech Ltd.) as the crystal nucleating agent, a poly(lactic acid) film was obtained in the same way as in Example 1, and the crystallization temperature was measured. The results are shown in Table 3.

Comparative Example 2

Aside from using 1 part by mass of the zinc phenylphosphonate obtained in Comparative Synthesis Example 1 as the crystal nucleating agent, a poly(lactic acid) film was obtained in the same way as in Example 1, and the crystallization temperature was measured. The results are shown in Table 3.

Comparative Example 3

Aside from using 0.23 part by mass of the zinc phenylphosphonate obtained in Comparative Synthesis Example 1 as the crystal nucleating agent, a poly(lactic acid) film was obtained in the same way as in Example 1, and the crystallization temperature was measured. The results are shown in Table 3.

Comparative Example 4

Aside from using 0.23 part by mass of the zinc phenylphosphonate obtained in Comparative Synthesis Example 1 and 0.77 part by mass of zinc oxide (JIS grade 2, available from HakusuiTech Ltd.) as the crystal nucleating agent, a poly(lactic acid) film was obtained in the same way as in Example 1, and the crystallization temperature was measured. The results are shown in Table 3.

Comparative Example 5

Aside from not adding a crystal nucleating agent, a poly(lactic acid) film was obtained in the same way as in Example 1, and the crystallization temperature was measured. The results are shown in Table 3.

TABLE 3

| Crystal nucleating agent | | PPA-Zn/ ZnO molar ratio | PPA-Zn content (pbm) | Crystallization temperature $T_C$ (° C.) |
|---|---|---|---|---|
| | Type | Amount added (pbm) | | |
| Example 1 | Synthesis Example 1 | 1 | 70/30 | 0.86 | 135.8 |
| Example 2 | Synthesis Example 2 | 1 | 50/50 | 0.73 | 136.0 |
| Example 3 | Synthesis Example 3 | 1 | 30/70 | 0.54 | 135.8 |
| Example 4 | Synthesis Example 4 | 1 | 10/90 | 0.23 | 135.9 |
| Example 5 | Synthesis Example 5 | 1 | 7/93 | 0.17 | 135.3 |
| Example 6 | Synthesis Example 6 | 1 | 5/95 | 0.13 | 135.0 |
| Example 7 | Synthesis Example 7 | 1 | 3/97 | 0.08 | 134.2 |
| Example 8 | Synthesis Example 8 | 1 | 1/99 | 0.03 | 133.5 |
| Example 30 | Synthesis Example 22 | 1 | 10/90 | 0.23 | 135.4 |
| Example 31 | Synthesis Example 23 | 1 | 10/90 | 0.23 | 135.5 |
| Comparative Example 1 | Zinc oxide | 1 | 0/100 | — | 120.6 |
| Comparative Example 2 | Comparative Synthesis Example 1 | 1 | 100/0 | 1.00 | 134.6 |
| Comparative Example 3 | Comparative Synthesis Example 1 | 0.23 | 100/0 | 0.23 | 133.8 |
| Comparative Example 4 | Comparative Synthesis Example 1 Zinc oxide | 0.23 0.77 | 10/90 | 0.23 | 134.0 |
| Comparative Example 5 | None | — | — | — | 109.2 |

Examples 25 to 29

Aside from using 1 part by mass of the zinc phenylphosphonate-containing zinc oxide obtained in Synthesis Examples 17 to 21 as the crystal nucleating agent, a poly(lactic acid) film was obtained in the same way as in Example 1, and the crystallization temperature was measured. The results are shown in Table 4.

TABLE 4

| Crystal nucleating agent | | Solvent used in synthesis | PPA-Zn/ZnO molar ratio | Crystallization temperature $T_C$ (° C.) |
|---|---|---|---|---|
| | Type | | | |
| Example 25 | Synthesis Example 17 | 50% by mass ethanol-water | 10/90 | 135.7 |
| Example 26 | Synthesis Example 18 | 75% by mass ethanol-water | 10/90 | 135.5 |
| Example 27 | Synthesis Example 19 | 90% by mass ethanol-water | 10/90 | 135.4 |
| Example 28 | Synthesis Example 20 | Ethanol | 10/90 | 133.3 |
| Example 29 | Synthesis Example 21 | 50% by mass methanol-water | 10/90 | 135.5 |
| Example 4 (Re-shown) | Synthesis Example 4 | Water | 10/90 | 135.9 |

Examples 9 to 16

In each example, a 5% by mass poly(lactic acid) solution was prepared by adding 1,900 parts by mass of chloroform to 100 parts by mass of poly(lactic acid) resin (U'z S-09, available from Toyota Motor Corporation) and dissolving the resin. One part by mass of the calcium phenylphosphonate-containing calcium carbonate obtained in Synthesis Examples 9 to 16 was added as the crystal nucleating agent to the entire amount of this solution. The crystal nucleating agent was dispersed in the solution by sonicating the resulting mixture for 30 minutes, stirring for 3 hours, then sonicating again for 30 minutes. The resulting solution was then cast onto a Petri dish and the solvent was removed at 50° C. on a hot plate, thereby giving a poly(lactic acid) film in which crystal nucleating agent has been dispersed. This sample was cut up into small pieces, and differential scanning calorimetry (DSC) was carried out (Diamond DSC, manufactured by PerkinElmer). Measurement was carried out by increasing the temperature to 200° C. at 10° C./min, holding the temperature at that level for 5 minutes, then cooling at 5° C./min. The crystallization temperature $T_C$ from the peak temperature of the exotherm which is attributable to poly(lactic acid) crystallization and is observed at the time of cooling was measured. The results are shown in Table 5.

Comparative Example 6

Aside from using 1 part by mass of calcium carbonate (Escalon #2300 (average particle size, 1.7 μm), available from Sankyo Seifun KK) as the crystal nucleating agent, a poly(lactic acid) film was obtained in the same way as in Example 9, and the crystallization temperature was measured. The results are shown in Table 5.

Comparative Example 7

Aside from using 1 part by mass of the calcium phenylphosphonate obtained in Comparative Synthesis Example 2 as the crystal nucleating agent, a poly(lactic acid) film was obtained in the same way as in Example 9, and the crystallization temperature was measured. The results are shown in Table 5.

Comparative Example 8

Aside from using 0.18 part by mass of the calcium phenylphosphonate obtained in Comparative Synthesis Example 2 as the crystal nucleating agent, a poly(lactic acid) film was obtained in the same way as in Example 9, and the crystallization temperature was measured. The results are shown in Table 5.

Comparative Example 9

Aside from using 0.18 part by mass of the calcium phenylphosphonate obtained in Comparative Synthesis Example 2 and 0.82 part by mass of calcium carbonate (Escalon #2300 (average particle size, 1.7 μm), available from Sankyo Seifun KK) as the crystal nucleating agent, a poly(lactic acid) film was obtained in the same way as in Example 9, and the crystallization temperature was measured. The results are shown in Table 5.

Comparative Example 10

Aside from not adding a crystal nucleating agent, a poly(lactic acid) film was obtained in the same way as in Example 9, and the crystallization temperature was measured. The results are shown in Table 5.

TABLE 5

| | Crystal nucleating agent | | | | Crystallization temperature (° C.) |
|---|---|---|---|---|---|
| | Type | Amount added (pbm) | PPA-Ca/CaCO$_3$ molar ratio | PPA-Ca content (pbm) | |
| Example 9 | Synthesis Example 9 | 1 | 70/30 | 0.82 | 127.3 |
| Example 10 | Synthesis Example 10 | 1 | 50/50 | 0.66 | 128.8 |
| Example 11 | Synthesis Example 11 | 1 | 30/70 | 0.46 | 129.1 |
| Example 12 | Synthesis Example 12 | 1 | 10/90 | 0.18 | 130.9 |
| Example 13 | Synthesis Example 13 | 1 | 7/93 | 0.13 | 126.1 |
| Example 14 | Synthesis Example 14 | 1 | 5/95 | 0.09 | 125.1 |
| Example 15 | Synthesis Example 15 | 1 | 3/97 | 0.06 | 125.1 |
| Example 16 | Synthesis Example 16 | 1 | 1/99 | 0.02 | 122.3 |
| Comparative Example 6 | Calcium carbonate | 1 | 0/100 | — | 119.2 |
| Comparative Example 7 | Comparative Synthesis Example 2 | 1 | 100/0 | 1.0 | 132.3 |
| Comparative Example 8 | Comparative Synthesis Example 2 | 0.18 | 100/0 | 0.18 | 123.4 |
| Comparative Example 9 | Comparative Synthesis Example 2 Calcium carbonate | 0.18 0.82 | 10/90 | 0.18 | 123.8 |
| Comparative Example 10 | None | — | — | — | 113.3 |

Examples 17 to 24

In each example, 1 part by mass of the calcium phenylphosphonate-containing calcium carbonate obtained in Synthesis Examples 9 to 16 was added as the crystal nucleating agent to 100 parts by mass of isotactic polypropylene (NOVATEC MA3, available from Japan Polypropylene Corporation), and the crystal nucleating agent was dispersed in the polypropylene resin by melt kneading at 185° C. for 5 minutes using a Labo Plastomill μ manufactured by Toyo Seiki Seisaku-Sho, Ltd. This sample was cut up into small pieces, and differential scanning calorimetry (DSC) was carried out (Diamond DSC, manufactured by PerkinElmer). Measurement was carried out by increasing the temperature to 200° C. at 10° C./min, holding the temperature at that level for 5 minutes, then cooling at 5° C./min. The crystallization temperature $T_C$ from the peak temperature of the exotherm which is attributable to polypropylene crystallization and is observed at the time of cooling was measured. The results are shown in Table 6.

Comparative Example 11

Aside from using 1 part by mass of calcium carbonate (Escalon #2300 (average particle size, 1.7 μm), available from Sankyo Seifun KK) as the crystal nucleating agent, a polypropylene sample was obtained in the same way as in Example 17, and the crystallization temperature was measured. The results are shown in Table 6.

Comparative Example 12

Aside from using 1 part by mass of the calcium phenylphosphonate obtained in Comparative Synthesis Example 2 as the crystal nucleating agent, a polypropylene sample was obtained in the same way as in Example 17, and the crystallization temperature was measured. The results are shown in Table 6.

Comparative Example 13

Aside from using 0.18 part by mass of the calcium phenylphosphonate obtained in Comparative Synthesis Example 2 as the crystal nucleating agent, a polypropylene sample was obtained in the same way as in Example 17, and the crystallization temperature was measured. The results are shown in Table 6.

Comparative Example 14

Aside from using 0.18 part by mass of the calcium phenylphosphonate obtained in Comparative Synthesis Example 2 and 0.82 part by mass of calcium carbonate (Escalon #2300 (average particle size, 1.7 μm), available from Sankyo Seifun KK) as the crystal nucleating agent, a polypropylene sample was obtained in the same way as in Example 17, and the crystallization temperature was measured. The results are shown in Table 6.

Comparative Example 15

Aside from not adding a crystal nucleating agent, a polypropylene sample was obtained in the same way as in Example 17, and the crystallization temperature was measured. The results are shown in Table 6.

TABLE 6

| | Crystal nucleating agent | | | | Crystallization |
|---|---|---|---|---|---|
| | Type | Amount added (pbm) | PPA-Ca/CaCO$_3$ molar ratio | PPA-Ca content (pbm) | temperature (° C.) |
| Example 17 | Synthesis Example 9 | 1 | 70/30 | 0.82 | 133.1 |
| Example 18 | Synthesis Example 10 | 1 | 50/50 | 0.66 | 132.8 |
| Example 19 | Synthesis Example 11 | 1 | 30/70 | 0.46 | 133.4 |
| Example 20 | Synthesis Example 12 | 1 | 10/90 | 0.18 | 133.2 |
| Example 21 | Synthesis Example 13 | 1 | 7/93 | 0.13 | 133.0 |
| Example 22 | Synthesis Example 14 | 1 | 5/95 | 0.09 | 132.4 |
| Example 23 | Synthesis Example 15 | 1 | 3/97 | 0.06 | 131.6 |
| Example 24 | Synthesis Example 16 | 1 | 1/99 | 0.02 | 129.9 |
| Comparative Example 11 | Calcium carbonate | 1 | 0/100 | — | 124.6 |
| Comparative Example 12 | Comparative Synthesis Example 2 | 1 | 100/0 | 1.0 | 134.2 |
| Comparative Example 13 | Comparative Synthesis Example 2 | 0.18 | 100/0 | 0.18 | 131.5 |
| Comparative Example 14 | Comparative Synthesis Example 2 Calcium carbonate | 0.18 0.82 | 10/90 | 0.18 | 131.6 |
| Comparative Example 15 | None | — | — | — | 123.4 |

As shown in FIGS. 1, 2, 3 and 4, the zinc phenylphosphonate-containing zinc oxide (FIG. 1) and the calcium phenylphosphonate-containing calcium carbonate (FIG. 3) obtained according to the production method of the present invention were confirmed to have a much finer shape than the conventional zinc phenylphosphonate (FIG. 2) and calcium phenylphosphonate (FIG. 4) obtained by reacting phenylphosphonic acid compounds with an equivalent amount of a metal salt or a metal oxide.

Also, as shown in Tables 3 to 6, poly(lactic acid) films produced with the white powder of zinc phenylphosphonate-containing zinc oxide (Examples 1 to 8), poly(lactic acid) films obtained with the white powder of calcium phenylphosphonate-containing calcium carbonate (Examples 9 to 16) or polypropylene samples (Examples 17 to 24), all of which were obtained according to the production method of the present invention, exhibited higher crystallization temperatures than in the comparative examples, even though the actual contents of zinc phenylphosphonate or calcium phenylphosphonate were equivalent to or lower than in the respective comparative examples. In addition, poly(lactic acid) films produced with the white powder of zinc phenylphosphonate-containing zinc oxide obtained by using ethanol-water or methanol-water as the solvent for the synthesis (Examples 25 to 27 and 29), exhibited higher crystallization temperatures than in the comparative examples, and poly(lactic acid) films produced with the white powder of zinc phenylphosphonate-containing zinc oxide obtained by using ethanol as the solvent (Example 28), exhibited crystallization temperatures comparable with that in the comparative examples.

Also, even when a poly(lactic acid) film (Comparative Example 4 or Comparative Example 9) or a polypropylene sample (Comparative Example 14) was produced with a powder obtained by simply mixing together a phenylphosphonic acid metal salt and a metal salt or a metal oxide, results were obtained which fell short of the crystallization temperature of the phenylphosphonic acid metal salt-containing metal salt or metal oxide (Examples 4, 12, 20) obtained by the production method of the present invention.

That is, results were obtained which indicated that the zinc phenylphosphonate-containing zinc oxide or the calcium phenylphosphonate-containing calcium carbonate used in these examples exhibited better performances as crystal nucleating agents than the conventional compounds obtained by reacting phenylphosphonic acid compounds with an equivalent amount of a metal salt or metal oxide.

From the above, results were obtained which indicate that the production method of the present invention is capable of providing crystal nucleating agents which have a high productivity while reducing the amount of petroleum-derived ingredients (e.g., phenylphosphonic acid).

Therefore, by adding a composition comprising a phenylphosphonic acid metal salt and surplus metal salt, surplus metal oxide or surplus metal hydroxide (a metal salt, metal oxide or metal hydroxide in which a phenylphosphonic acid metal salt is dispersed) as a crystal nucleating agent, the crystallization rate of the thermoplastic resin can be increased and a thermoplastic resin composition having an excellent heat resistance and processability can be provided.

What is claimed is:
1. A method for producing a phenylphosphonic acid metal salt composition, comprising reacting a phenylphosphonic acid compound (a) of formula [1]

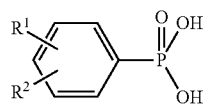

in which $R^1$ and $R^2$ are independently of each other hydrogen atom, $C_{1-10}$alkyl or $C_{1-10}$alkoxycarbonyl, with a metal salt, metal oxide or metal hydroxide (b) that is present in an amount beyond the equivalent, wherein a molar ratio of the metal salt, metal oxide or metal hydroxide (b) to the phenylphosphonic acid compound (a) for the reaction is from 100:0.01 to 100:30,
wherein the phenylphosphonic acid metal salt composition contains phenylphosphonic acid metal salt, and a surplus amount of the metal salt, the metal oxide or the metal hydroxide (b).

2. The method according to claim 1, wherein the reaction of the phenylphosphonic acid compound (a) with the metal salt, metal oxide or metal hydroxide (b) is carried out in the presence of particles of the metal salt, metal oxide or metal hydroxide (b).

3. The method according to claim 1, wherein the reaction of the phenylphosphonic acid compound (a) with the metal salt, metal oxide or metal hydroxide (b) is carried out in a solvent that hardly dissolves the metal salt, metal oxide or metal hydroxide (b).

4. The method according to claim 1, wherein the metal of the metal salt, metal oxide or metal hydroxide (b) is zinc, calcium or manganese.

5. The method according to claim 4, wherein the metal of the metal salt, metal oxide or metal hydroxide (b) is zinc or calcium.

6. The method according to claim 5, wherein the metal salt, metal oxide or metal hydroxide (b) is zinc oxide or calcium carbonate.

7. The method according to claim 1, wherein the molar ratio of the metal salt, metal oxide or metal hydroxide (b) to the phenylphosphonic acid compound (a) for the reaction is from 100:2 to 100:30.

8. A method for producing a phenylphosphonic acid metal salt composition, comprising reacting a phenylphosphonic acid compound (a) of formula [1]

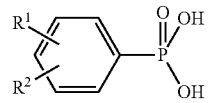

in which $R^1$ and $R^2$ are independently of each other hydrogen atom, $C_{1-10}$alkyl or $C_{1-10}$alkoxycarbonyl, with a metal salt, metal oxide or metal hydroxide (b) that is present in an amount beyond the equivalent,
wherein the phenylphosphonic acid metal salt composition contains phenylphosphonic acid metal salt, and a surplus amount of the metal salt, the metal oxide or the metal hydroxide (b), and
wherein the reaction results in the phenylphosphonic acid metal salt having an average size or average thickness of from 0.05 μm to 1 μm without application of any shear to the phenylphosphonic acid metal salt.

9. The method according to claim 1, wherein the reaction is conducted at a temperature of 30° C. or less.

10. The method according to claim 8, wherein the reaction is conducted at a temperature of 30° C. or less.

* * * * *